United States Patent [19]

Nakano et al.

[11] Patent Number: 5,076,981

[45] Date of Patent: Dec. 31, 1991

[54] PROCESS FOR PRODUCTION OF ALUMINUM NITRIDE SINTERED BODY

[75] Inventors: Kazuhiko Nakano; Michio Shinohara, both of Ibaraki; Mitsutoshi Murase, Ehime, all of Japan

[73] Assignee: Sumitomo Chemical Co., Ltd., Osaka, Japan

[21] Appl. No.: 646,476

[22] Filed: Jan. 25, 1991

Related U.S. Application Data

[63] Continuation of Ser. No. 447,461, Dec. 7, 1989, abandoned.

[30] Foreign Application Priority Data

Dec. 7, 1988 [JP] Japan .................. 63-310495
Dec. 7, 1988 [JP] Japan .................. 63-310496

[51] Int. Cl.$^5$ ............................................ C04B 35/58
[52] U.S. Cl. ...................................... 264/65; 501/96; 501/98
[58] Field of Search ..................... 501/96, 98; 264/65

[56] References Cited

U.S. PATENT DOCUMENTS 4,650,777 5/1987 Kurokawa et al. ............. 501/96
4,746,637 5/1988 Kasori et al. ................... 501/98

FOREIGN PATENT DOCUMENTS 47-18655 5/1972 Japan .
58-49510 11/1983 Japan .
61-209959 9/1986 Japan .

OTHER PUBLICATIONS

N. Kuramoto et al., "Transparent ALN Ceramics"; Journal of Materials Science Letters, vol. 13, pp. 471–479; 1984.

*Primary Examiner*—James Derrington
*Attorney, Agent, or Firm*—Sughrue, Mion, Zinn, Macpeak & Seas

[57] ABSTRACT

A process for producing an aluminum nitride sintered body is disclosed, comprising mixing an aluminum nitride powder with (a) a calcium compound and (b) a copper compound, and, if desired, (c) a yttrium compound as sintering aids; molding the mixture; and sintering the molded article in a non-oxidative atmosphere. The resulting sintered body has a high density (3.10 g/cm$^3$ or higher) and a high thermal conductivity (110 W/mK or higher) even by sintering at a low temperature (1500° to 2000° C.).

9 Claims, No Drawings

PROCESS FOR PRODUCTION OF ALUMINUM NITRIDE SINTERED BODY

This is a continuation of application Ser. No. 07/447,461 filed Dec. 7, 1989, now abandoned.

FIELD OF THE INVENTION

This invention relates to a process for production of an aluminum nitride sintered body and more particularly, to a process for producing an aluminum nitride sintered body having a high density and satisfactory thermal conductivity by sintering at a temperature lower than that in conventional techniques.

BACKGROUND OF THE INVENTION

Aluminum nitride has been attracting attention as a packaging material or a substrate material best adapted for heat dissipation because of its high thermal conductivity, excellent electrical characteristics, such as insulation resistance, dielectric strength, and dielectric constant, and excellent mechanical characteristics, such as strength.

Production of an aluminum nitride sintered body having excellent thermal conductivity requires molding of an aluminum nitride powder followed by densely sintering.

Since aluminum nitride by itself is hardly sintered under atmospheric pressure, pressureless sintering of aluminum nitride has conventionally be carried out with the aid of an oxide, such as CaO and $Y_2O_3$, taking advantage of the reaction between such a sintering aid and $Al_2O_3$ present on the aluminum nitride skin layer to achieve denseness.

For example, JP-B-47-18655 (the term "JP-B" as used herein means an "examined published Japanese patent application") discloses addition of $Y_2O_3$ for obtaining a dense sintered body, and JP-B-58-49510 proposes addition of CaO, BaO, SrO, etc. to obtain a dense aluminum nitride sintered body having a relative density of 98.5% or more.

In the case of adding $Y_2O_3$ for obtaining a dense sintered body having high thermal conductivity by pressureless sintering, a high temperature of 1800° C. or even more should be required. Also in the case of adding CaO, pressureless sintering is usually carried out at a high temperature of 1700° C. or more.

Alumina which is currently employed as an IC packaging material or a substrate material is usually sintered at a temperature of from 1500° to 1600° C. to obtain denseness. Compared with this temperature, the sintering temperature required for obtaining an aluminum nitride sintered body with the aid of the above-described sintering aid is considerably higher, and this has been a bar to reduction of cost for production of an aluminum nitride sintered body.

In this connection, it has been proposed to add an oxide or fluoride of a rare earth metal and an oxide or fluoride of an alkaline earth metal to make it feasible to densify at 1600° C. as disclosed in JP-A-61-209959 (the term "JP-A" as used herein means an "unexamined published Japanese patent application"). However, the thermal conductivity attained by this process is about 100 W/mk at the highest.

SUMMARY OF THE INVENTION

An object of this invention is to provide a process for producing a dense aluminum nitride sintered body having high thermal conductivity by sintering at a temperature lower than that in the conventional processes.

The present invention relates to a process for producing an aluminum nitride sintered body comprising mixing an aluminum nitride powder with (A) (a) a calcium compound and (b) a copper compound or (B) (a) a calcium compound, (b) a copper compound, and (c) a yttrium compound, the amount of each of the calcium compound and copper compound being from 0.01 to 3% by weight, on a CaO or CuO basis, based on the aluminum nitride, with a (b)/(a) molar ratio on a CuO/CaO basis being not more than 1, and the amount of the yttrium compound being from 0.1 to 10% by weight, on a $Y_2O_3$ basis, based on the aluminum nitride; molding the mixture; and sintering the molded article in a non-oxidative atmosphere.

DETAILED DESCRIPTION OF THE INVENTION

The aluminum nitride powder which can be used in the present invention is not particularly limited in process for preparation, but a fine powder of high purity is preferred. It is preferable to use a powder having an average particle diameter of not greater than 4.0 μm. In particular, for the purpose of densifying at 1600° C. or lower temperatures, it is desirable, if possible, to use a fine powder having an average particle diameter of not greater than 2.0 μm.

Calcium and copper compounds which can be used as sintering aids include oxides, hydroxides, carbonates, sulfates, nitrates, acetates, oxalates, halides, sulfides, and higher fatty acid salts of calcium or copper.

Yttrium compounds which can be used as sintering aids include oxides, nitrides, oxalates, and halide of yttrium.

Composite compounds containing at least two elements selected from calcium, copper and yttrium, or composite compounds containing these elements and aluminum may also be employed as sintering aids.

While any kind of substances may be used as a sintering aid as far as calcium, copper or yttrium is in a compound form, compounds free from water of crystallization are preferred.

Specific examples of suitable sintering aids are CaO, $Ca(OH)_2$, $CaCO_3$, $CaSO_4 \cdot 2H_2O$, $Ca(NO_3)_2 \cdot 4H_2O$, $Ca(CH_3COO)_2$, $Ca(COO)_2 \cdot H_2O$, $CaF_2$, CaS, $Ca(CH_3(CH_2)_{16}COO)_2$, CuO, $Cu_2O$, $Cu(OH)_2$, $CuCO_3 \cdot Cu(OH)_2 \cdot H_2O$, $CuSO_4$, $Cu(NO_3)_2 \cdot 3H_2O$, $Cu(CH_3COO)_2 \cdot H_2O$, $Cu(COO)_2$, $CuF_2$, CuS, $Cu(CH_3(CH_2)_{16}COO)_2$, $Y_2O_3$, $Y(NO_3)_3 \cdot 9H_2O$, $Y(COO)_3 \cdot H_2O$, $YF_3 \cdot 0.5H_2O$, $CuO \cdot 2CaO$, $Ca_2AlO_4$, and $CaYAlO_4$.

In one embodiment, the present invention provides a process for producing an aluminum nitride sintered body comprising mixing an aluminum nitride powder with (a) a calcium compound, (b) a copper compound, and (c) a yttrium compound, and the amount of each of the calcium compound and copper compound being from 0.01 to 3% by weight, on a CaO or CuO basis, based on the aluminum nitride, with a (b)/(a) molar ratio on a CuO/CaO basis being not more than 1, the amount of the yttrium compound being from 0.1 to 10% by weight, on a $Y_2O_3$ basis, based on the aluminum nitride; molding the mixture; and sintering the molded article in a non-oxidative atmosphere.

According to the present invention, an aluminum nitride sintered body having a density of 3.10 g/cm³ or higher and a high thermal conductivity can be obtained even by sintering at a lower temperature as compared with the conventional technique.

The reason why the aluminum nitride sintered body according to the present invention is densified even at a low temperature to exhibit high thermal conductivity has not yet been elucidated, but the following assumption could be made. Densification of aluminum nitride by pressureless sintering is believed to proceed via a liquid phase. Therefore, it appears that addition of a substance which is capable of forming a liquid phase in a lower temperature range as a sintering aid would lower the temperature at which densification of aluminum nitride initiates. It is thus considered that $Al_2O_3$ on the surface of the aluminum nitride powder is dissolved in the liquid phase formed by the sintering aid whereby densification proceeds even at a low temperature.

When an aluminum nitride powder is mixed with a calcium compound and a copper compound and further with a yttrium compound, the reaction with $Al_2O_3$ in the oxidized skin layer of the aluminum nitride powder seems to proceed more smoothly to form a Ca—Cu—Y—Al—O system liquid phase from which densification starts at a lower temperature.

The sintering aid compounds to be added preferably have a particle size as fine as possible. When, in particular, in using a compound insoluble or sparingly soluble in a solvent used for mixing with an aluminum nitride powder, it is generally preferable to use fine particles having an average particle diameter of not greater than 5.0 μm.

The calcium compound and copper compound are added each preferably in an amount of from 0.01 to 3% by weight, on a CaO or CuO basis, based on the aluminum nitride powder, with a molar ratio on a CuO/CaO basis being not more than 1. The yttrium compound is added in an amount of from 0.1 to 10% by weight, on a $Y_2O_3$ basis, based on the aluminum nitride powder.

If the amount of each sintering aid is outside the above-recited range, it is difficult to obtain a dense sintering body by pressureless sintering. If any dense sintered body may be obtained, sufficiently high thermal conductivity cannot be attained.

A preferred amount of each of the calcium compound and copper compound to be added is from 0.05 to 2% by weight, on a CaO or CuO basis, based on the aluminum nitride, with the molar ratio on a CuO/CaO basis of not more than 1. A preferred amount of the yttrium compound to be added is from 0.5 to 5% by weight, on a $Y_2O_3$ basis, based on the aluminum nitride.

Mixing of the aluminum nitride powder with (A) the calcium compound and copper compound or with (B) the calcium compound, copper compound and yttrium compound can be carried out by dry blending or wet blending using a non-aqueous solvent, e.g., alcohols. Usually, wet blending using a non-aqueous solvent is preferred.

Where mixing is performed by wet blending, a known binder, e.g., polyvinyl butyral, polyvinyl alcohol, and a polyacrylic ester, is usually added in order to facilitate the subsequent molding step.

In addition to the binder, various additives, such as dispersing agents, plasticizers, and wetting agents, are usually added. The kinds and amounts of these additives are selected appropriately depending on the molding method employed.

Apparatus for mixing include generally employed apparatus, such as a ball mill and various kneaders. If desired, the resulting mixture is dried and granulated or formulated into a sludge or slurry, etc. according to the molding method.

Molding methods include dry processes using a hydraulic press, a cold isostatic press, etc. and wet processes, e.g., a doctor blade process and an extrusion process.

The process of the present invention can also be applied to hot pressing in which molding and sintering are carried out simultaneously.

The resulting molded article is then put in a container called as a box, which is made of graphite, boron nitride, aluminum nitride, alumina, etc. Where sintering is conducted at high temperatures of 1700° C. or higher, a box made of graphite, boron nitride or aluminum nitride is preferred. Sintering may also be carried out by a so-called powder bed process in which the molded article is embedded in a powder mainly comprising aluminum nitride and sintered.

In order to prevent aluminum nitride from oxidation during sintering, it is necessary to conduct sintering in a non-oxidative atmosphere. The non-oxidative atmosphere includes nitrogen, argon, a mixed gas of nitrogen and hydrogen, and a mixed gas of nitrogen and argon, with a nitrogen atmosphere being the most preferred in view of production cost incurred and ease in handling of the apparatus.

The sintering temperature is selected from the range of from 1500° to 2000° C. and, in practice, preferably from 1550° to 1800° C. The rate of temperature rise is not particularly limited and is usually selected from 1° to 5° C./min. The retention time at the sintering temperature is selected from the range of from 2 to 20 hours so that the resulting aluminum nitride sintered product may have a density of 3.10 g/cm$^3$ or more. A preferred retention time is from 2 to 8 hours.

The resulting aluminum nitride sintered body preferably has a density of 3.10 g/cm$^3$ or more. Even when the density of the sintered body is less than 3.10 g/cm$^3$, the sintered body apparently looks dense but contains many voids, failing to exhibit high thermal conductivity.

The present invention is now illustrated in greater detail with reference to Examples, but it should be understood that the present invention is not deemed to be limited thereto.

EXAMPLE 1

In a 250 ml polyethylene-made pot were charged 19.66 g of an aluminum nitride (AlN) powder obtained by reductive nitriding of alumina (oxygen content: 1.3%; iron content: 10 ppm; silicon content: 60 ppm; titanium content: 16 ppm; average particle diameter: 1.4 μm), 0.357 g of a calcium carbonate ($CaCO_3$) ("Hakuenka CCR" produced by Shiraishi Calcium Co., Ltd.) and 0.14 g of cupric oxide (CuO) (GR grade, produced by Nakarai Chemical Co., Ltd.), and 25 g of n-butanol, 4.0 g of an acrylic binder ("CB-1" produced by Sanyo Chemical Industries, Ltd.), and 1.0 g of a dispersing agent ("Seramo D-18" produced by Dai-ichi Kogyo Yakuhin Co., Ltd.) were added thereto. The mixture was wet blended in a ball mill using nylon-coated iron balls having a diameter of 15 mm at a revolution rate of 60 rpm for 4 hours.

The resulting slurry was dried and lightly ground in a mortar made of agate to prepare a sintering powder.

The sintering powder was put in a mold, hydraulically pressed under a pressure of 300 kg/cm$^2$, and then molded by a cold isostatic press under a pressure of 1500 kg/cm² to obtain a molded article having a diameter of 13 mm and a thickness of 10 mm.

The molded article was put in a graphite container, embedded in a mixed powder of aluminum nitride and boron nitride and sintered pressurelessly at a temperature of 1550° C., 1600° C., 1700° C. or 1800° C. in a nitrogen atmosphere for 5 hours. The density and thermal conductivity of the resulting sintered body are shown in Table 1 below. Specimens for the thermal conductivity measurement were prepared by slicing the sintered body to a diameter of 10 mm and a thickness of 3 mm, vacuum depositing gold on the slice, and spraying carbon thereon.

TABLE 1

| Run No. | Sintering Temperature (°C.) | Fired Density (g/cm³) | Thermal Conductivity (W/mK) |
|---|---|---|---|
| 1-1 | 1550 | 3.12 | 112 |
| 1-2 | 1600 | 3.22 | 125 |
| 1-3 | 1700 | 3.24 | 150 |
| 1-4 | 1800 | 3.25 | 155 |

EXAMPLE 2

A sintering powder was prepared in the same manner as in Example 1, except for changing the amounts of AlN, $CaCO_3$ and CuO powders added as shown in Table 2 below.

Each of the sintering powders was molded in the same manner as in Example 1 and then sintered pressurelessly at 1600° C. for 5 hours.

The density and thermal conductivity of the resulting sintered body are shown in Table 2.

TABLE 2

| Run No. | Composition of Sintered Powder AlN (g) | $CaCO_3$ (g) | CuO (g) | Fired Density (g/cm³) | Thermal Conductivity (W/mK) |
|---|---|---|---|---|---|
| 2-1 | 19.3 | 0.4 | 0.3 | 3.21 | 122 |
| 2-2 | 19.0 | 0.8 | 0.2 | 3.19 | 117 |
| 2-3 | 18.6 | 0.9 | 0.5 | 3.20 | 120 |
| 2-4 | 19.5 | 0.3 | 0.2 | 3.23 | 128 |
| 2-5 | 19.8 | 0.15 | 0.05 | 3.24 | 132 |

EXAMPLE 3

A sintering powder was prepared and molded in the same manner as in Example 1, except for using 18.9 g of the same AlN powder as used in Example 1, 0.36 g of the same $CaCO_3$ powder as used in Example 1, 0.14 g of the same CuO powder as used in Example 1, and 0.6 g of a $Y_2O_3$ powder (produced by Shin-Etu Chemical Co., Ltd.). The molded article was sintered pressurelessly in a nitrogen atmosphere at a temperature of 1550° C., 1600° C., 1700° C. or 1800° C. for 5 hours. The density and thermal conductivity of each of the resulting sintered bodies are shown in Table 3 below.

TABLE 3

| Run No. | Sintering Temperature (°C.) | Fired Density (g/cm³) | Thermal Conductivity (W/mK) |
|---|---|---|---|
| 3-1 | 1550 | 3.16 | 118 |
| 3-2 | 1600 | 3.28 | 142 |
| 3-3 | 1700 | 3.28 | 163 |
| 3-4 | 1800 | 3.28 | 198 |

EXAMPLE 4

A sintering powder was prepared in the same manner as in Example 3, except for changing the amounts of AlN, $CaCO_3$, CuO and $Y_2O_3$ powders added as shown in Table 4 below.

Each of the resulting sintering powders was molded in the same manner as in Example 1 and then sintered pressurelessly at 1600° C. for 5 hours. The density and thermal conductivity of the resulting sintered body are shown in Table 4.

TABLE 4

| Run No | Composition of Sintering Powder AlN (g) | $CaCO_3$ (g) | CuO (g) | $Y_2O_3$ (g) | Fired Density (g/cm³) | Thermal Conductivity (W/mK) |
|---|---|---|---|---|---|---|
| 4-1 | 19.2 | 0.3 | 0.2 | 0.3 | 3.24 | 132 |
| 4-2 | 18.5 | 0.5 | 0.3 | 0.7 | 3.26 | 138 |
| 4-3 | 18.0 | 0.9 | 0.5 | 0.6 | 3.27 | 126 |
| 4-4 | 19.0 | 0.2 | 0.2 | 0.6 | 3.28 | 149 |
| 4-5 | 19.2 | 0.1 | 0.1 | 0.6 | 3.28 | 147 |

COMPARATIVE EXAMPLE 1

A sintering powder prepared by mixing the same AlN powder as used in Example 1 with 3% by weight of the same $Y_2O_3$ powder as used in Example 3 was molded and sintered in the same manner as in Example 1. The density and thermal conductivity of each of the resulting sintered bodies are shown in Table 5 below.

TABLE 5

| Run No. | Sintering Temperature (°C.) | Fired Density (g/cm³) | Thermal Conductivity (W/mK) |
|---|---|---|---|
| 5-1 | 1550 | 2.43 | 38 |
| 5-2 | 1600 | 2.87 | 68 |
| 5-3 | 1700 | 2.97 | 87 |
| 5-4 | 1800 | 3.28 | 190 |

While the invention has been described in detail and with reference to specific embodiments thereof, it will be apparent to one skilled in the art that various changes and modifications can be made therein without departing from the spirit and scope thereof.

What is claimed is:

1. A process for producing an aluminum nitride sintered body comprising mixing an aluminum nitride powder with (a) from 0.01 to 3% by weight, on a CaO basis, of a calcium compound and (b) from 0.01 to 3% by weight, on a CuO basis, of a copper compound, with a (b)/(a) molar ratio on a CuO/CaO basis being not more than 1 and wherein each of said calcium and copper compounds is selected from the group consisting of oxides, hydroxides, carbonates, sulfates, nitrates, acetates, oxalates, halides, sulfides, and higher fatty acid salts of calcium or copper; molding the mixture; and sintering the molded article in a non-oxidative atmosphere.

2. A process for producing an aluminum nitride sintered body comprising mixing an aluminum nitride powder with (a) from 0.01 to 3% by weight, on a CaO basis, of a calcium compound, (b) from 0.01 to 3% by weight, on a CuO basis, of a copper compound, with a (b)/(a) molar ratio on a CuO/CaO basis being not more than 1 and wherein each of said calcium and copper compounds is selected from the group consisting of oxides, hydroxides, carbonates, sulfates, nitrates, acetates, oxalates, halides, sulfides, and higher fatty acid salts of calcium or copper; and (c) from 0.1 to 10% by weight, on a $Y_2O_3$ basis, of a yttrium compound; molding the mixture; and sintering the molded article in a non-oxidative atmosphere.

3. A process as claimed in claim 1, wherein said sintering is carried out at a temperature of from 1500° to 2000° C.

4. A process as claimed in claim 2, wherein said sintering is carried out at a temperature of from 1500° to 2000° C.

5. A process as claimed in claim 1, wherein said sintering is carried out for a retention time of from 2 to 20 hours.

6. A process as claimed in claim 2, wherein said sintering is carried out for a retention time of from 2 to 20 hours.

7. A process as claimed in claim 2, wherein said yttrium compound is selected from the group consisting of oxides, hydroxides, nitrates, oxalates, and halides of yttrium.

8. A process as claimed in claim 1, wherein said aluminum nitride powder has an average particle diameter of not greater than 4.0 μm.

9. A process as claimed in claim 2, wherein said aluminum nitride powder has an average particle diameter of not greater than 4.0 μm.

* * * * *